United States Patent [19]

Ruzicka et al.

[11] 4,177,677

[45] Dec. 11, 1979

[54] SAMPLE SUPPLY TO AUTOMATIC ANALYZERS

[75] Inventors: Jaromir Ruzicka, Naerum; Elo H. Hansen, Lyngby, both of Fed. Rep. of Germany

[73] Assignee: Bifok AB, Sollentuna, Sweden

[21] Appl. No.: 832,741

[22] Filed: Sep. 12, 1977

[30] Foreign Application Priority Data

Sep. 13, 1976 [SE] Sweden .............................. 7610110

[51] Int. Cl.² .............................................. G01N 1/18
[52] U.S. Cl. ............................ 73/422 GC; 23/230 R; 422/82; 422/100
[58] Field of Search ............. 23/230 R, 230 B, 253 R, 23/259; 73/423 A, 422 GC; 422/63, 100, 82

[56] References Cited

U.S. PATENT DOCUMENTS

| | | | |
|---|---|---|---|
| 3,615,234 | 10/1971 | Ludvigsen | 23/253 R |
| 3,698,870 | 10/1972 | DeJong | 23/253 R |
| 3,876,374 | 4/1975 | Burns | 23/253 R X |
| 3,933,430 | 1/1976 | Hare | 23/230 B X |
| 3,961,534 | 6/1976 | Gundelfinger | 73/422 GC |
| 4,007,638 | 2/1977 | Irwin et al. | 73/423 A X |
| 4,013,413 | 3/1977 | Stewart et al. | 23/253 R X |
| 4,018,565 | 4/1977 | Fletcher et al. | 23/253 R |
| 4,022,575 | 5/1977 | Hansen et al. | 23/230 R |
| 4,049,381 | 9/1977 | Burns et al. | 23/253 R X |

OTHER PUBLICATIONS

L. T. Skeggs, An Automatic Method For Colorimetric Analysis, Amer. J. Clin. Pathol., vol. 28, pp. 311-322 (1957).

*Primary Examiner*—Joseph Scovronek
*Attorney, Agent, or Firm*—Finnegan, Henderson, Farabow & Garrett

[57] ABSTRACT

A method and an apparatus for supplying samples to a flowing continuous carrier solution for automatic analysis whereby a measured sampling conduit with a predetermined length and volume is alternately coupled to an intake conduit for the sample and the path of the flowing carrier solution. The sample circuit includes a sample container, an intake tube, the sample conduit valves and a pump, and the carrier flow circuit includes an inlet tube, a pump, a conduit, valves, a shunt conduit, an outlet conduit and an outlet, and by means of the valves, the sampling conduit is connected into and out of the carrier flow circuit parallel to the shunt conduit.

4 Claims, 1 Drawing Figure

U.S. Patent  Dec. 11, 1979  4,177,677
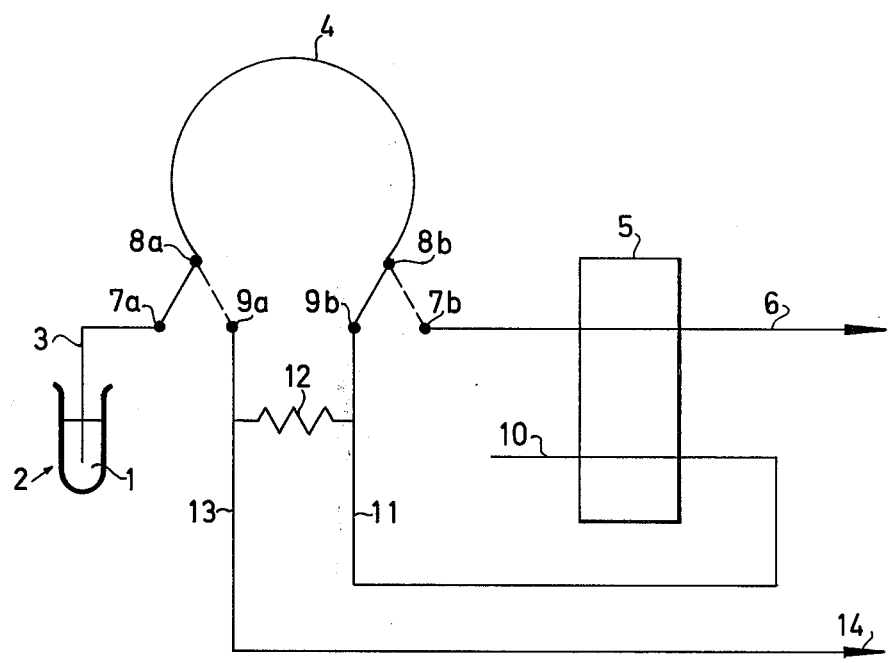

SAMPLE SUPPLY TO AUTOMATIC ANALYZERS

The present invention relates to automatic analysis arrangements and especially the supply of samples to the same.

The constantly increasing need for analyses within the medical, argicultural, pharmaceutical and several other fields has given rise to the development of a great number of different apparati for automatic analysis. The advantages therewith are increased precision, reduced cost per sample, and the great reliability of the automated equipment. The main development is now directed towards simplifying the analysis apparati and increasing their capacity.

The automatic analyzers can be divided into two groups. batch analyzers and continuous analyzers.

In batch analyzers, each sample is placed in an individual container and remains there during the entire analysis. The container is transported through the apparatus on a movable band or the like, reagents are added at predetermined times and finally, when the sample reaches the readout unit, a spectro-photometer, flame photometer, etc., it is drawn into a cell where measuring takes place. As the individual samples are totally separated throughout the entire process, a high analysis speed of more than 150 samples per hour can be achieved without risk of intermixture or mutual pollution of the samples. The disadvantages of batch analyzers are their complex movable parts which are worn down during use, and that problems can arise with washing or disposal of the containers after use. Furthermore, adaptability is poorer than in continuous analyzers.

In the continuous analyzers, the samples are drawn successively from the individual containers into a hose or tube in which the samples are moved until the analysis is terminated. In this manner, the samples become a continuous liquid flow into which reagents are continuously added at certain flow speeds at predetermined points. The treated liquid flow finally reaches the measuring cell, for example, in a spectrometer, where the quantitative measuring takes place and the signal is continuously registered. The transport of all the liquids in the continuous analyzers is controlled by a pump which also takes care of transport of the samples out of the analyzer.

The greatest advantage of the continuous analyzers is their simplicity and their adaptability which allows a simple programming of the liquid flow which can, for example, be split up for several different analyses. The disadvantages are primarily the potential possibility of intermixing, and, thus, air bubbles were introduced into the liquid flow whereby the continuous analysis was made practically possible; L. T. Skeggs, Am. J. Clin. Pathol., 28 (1957), page 311.

The task of the air bubble is to segment the flow and prevent intermixing of the samples in the conduits of the continuous analyzer, that is, to reduce the risk for pollution. The analysis speed amounts to up to approx. 100 samples per hour, even if 60 samples is the normal speed. Faster sequences can hardly be achieved as a state of continuity must be achieved for each individual measurement.

In studies of the continuous systems and the kinetic parameters for such systems, it has been found that all of the falling and rising curve branches in a given system have identical shape. Thus, it is not necessary to achieve the state of continuity as long as the sample is added to the continuously moving flow during an exactly fixed period of time. This precision of sample supply has, however, been impossible to achieve in commercial systems where sampling is achieved by a peristaltic pump which draws the samples from their individual containers and thereafter pumps them further through the system where, after segmentation by means of air bubbles at predetermined points, the samples are supplied with reagent solutions for the special analyses. The reasons for the deficient accuracy are (a) difficulties with exact time setting for movement of the sample tube from the sampling position to the washing position, and that the level of the liquid sample in all of the sample containers must be identical as, otherwise, varying amounts of air and, thus, samples are added to the sampling tube, (b) irregularities in the pumping effect of the peristaltic pump which are due to the distance between the rollers which press against the tubes, said irregularities appearing as periodic pulsations, and (c) the presence of the air bubbles which, aside from segmenting the flow, also give rise to pulsations due to the compressability of the air.

A new analyzer which functions without such segmenting air bubbles is described in U.S. Pat. No. 4,022,575, which is based on discrete injection of carefully-defined sample volumes in a continuous reagent flow. This injection takes place during an exactly-defined short period of time and provides geometrically well-defined segments of sample solution in the liquid flow which thereafter continue towards the detector unit. This technique has made it possible to achieve a reproducibility in the measurements which is better than plus or minus 1% and to attain a speed of up to 180 samples per hour. Furthermore, only very small sample volumes, 0.5 ml or less, are required as this instantaneous sample addition provides well-defined narrow sample segments which accordingly result in well marked detector signals.

For the sample addition, it has been found to be suitable to carry out the instantaneous discrete sample addition with an injection syringe which simultaneously serves as a pipette for measuring the sample volume. The injection needle is stuck through the wall of an elastic hose at a determined point in time and the sample is injected into the carrier flow through the hose. Mechanical arrangements for expediting insertion and injection can easily be made, but surprisingly enough, manual sample addition has been found to be very satisfactory.

The analyzer and its parameter are explained in detail in our above-mentioned U.S. patent specification.

A need for further developement has now been shown to exist. The greatest use of the automatic analyzer has previously been within the agricultural field, but its increased use within the medical field has increasingly emphasized the need for analysis of very small sample amounts. Consequently, an automatic analyzer in a clinical laboratory must be able to work with sample volumes between 200 and 20 $\mu$l while maintaining the same reproducibility and accuracy as in larger samples. The analysis speed must also be increased further. The present invention now relates to an improved sample supply. The advantage of manual injection has been its simplicity, and as long as a sufficient amount of sample material exists and a restricted number of samples are to be injected, the process is fully satisfactory. However, disposable syringes of 1 ml are not sufficiently exact for injections of samples of less than 200 μl, nor has the use of spring-loaded microsyringes been sufficient. According to the present invention, an automatic sample addition method has now been achieved in which the sample amount to a large extent can be varied in a simple manner by means of varying the volume of a measured sampling conduit. The method and device according to the invention have also been shown to be able to be advantageously used for commercial automatic analyzers having segmented flow.

The invention shall be described in more detail below in connection with the accompanying drawing which shows a schematically drawn automated sample supplying device according to the invention.

The liquid sample 1 is drawn from the sample container 2 through a tube 3 into a measured sampling conduit 4 of a predetermined volume by a pump 5. The surplus of the sample is flushed out through the conduit 6. During sampling, the connections 7a-8a, 7b-8b are open and connections 8a-9a, 8b-9b are closed, whereby the carrier flow 10 which is fed in by the pump 5 through the tube 11 is forced by the shunt conduit 12 out to conduit 13 to the analyzer 14 (not shown here). When the sampling conduit 4 has been filled, connections 8a-9a and 8b-9b are opened while connections 7a-8a and 7b-8b are closed. As shunt conduit 12 is designed so that it has much greater flow resistance than the conduit 4, the sample is pressed into the conduit 13 for the carrier flow to the analyzer 14 as a well-defined plug of known volume. Alteration of the length and inner diameter of the sampling conduit 4, which is made of polyethylene tubing, to alter the volume of the sample plug and of the shunt conduit 12 is very simple as the conduits 4, 12 are made as replaceable parts. Adaptability of the sampling conduit and its use in connection with fully automated sampling by means of combination with a sample carousel has also been done. The connections between the sampling conduit 4 and the different conduits pass through magnetic valves 7a and b, 8a and b and 9a and b, and the system is controlled by synchronized impulses to the sample carousels and the magnetic valves. The valves 7b, 8b, 9b, can consist of six simple one-way valves and be both manual or automatic, that is, electric, pneumatic, etc., but it has been found to be most advantageous to either use two three-way valves or a single four-way valve which, in one of its positions, couples the sampling conduit in between the sample container and the pump, and which, in its other position, couples the sampling conduit into the carrier flow circuit.

By means of the subduing effect from the shunt conduit 12, the jerky changes in the carrier flow which are characteristic for manual injection are avoided. Thus, several samples can be supplied to the carrier flow in close succession without disadvantageous disturbances in the flow parameters when a slow chemical reaction requires a long conduit. The reproducible injection of microvolumes is, furthermore, not only important as regards economizing with the sample material, but also allows an often-required automated dilution of the sample material.

The sample supply according to the invention has been used in determining inorganic phosphate and chloride in blood serum as these compounds represent two extremes as regards concentration in blood, approx. 100 meqv Cl/l for chlorine and 3.5 mgP/100 ml for phosphate in normal serum. Both of these measurements are normally made on serum samples subjected to dialysis.

It is important that the dialysis does not alter the geometry of the sample plug which is formed during injection, which means that the dialysable material shall form an identical but diluted and protein-free sample plug on the other side of the dialysis membrane which is moved forward with the recipient flow. The automated sample dilution must go up to 1:100 having a reproducibility of repeated injections of less than 1%.

Comparative tests between manual injection and automatic injection has been carried out on 5 serum samples, Auto-ref, Moni-trol I, Moni-trol II, Technicon SMA 2 and Serum Pool, and the values are based on Moni-trol I as an internal standard having the value 102 meqv Cl/l.

Table 1 shows the measurement of chlorine with manual and automatic sample supply both with and without dialysis. Samples of 200 μl were used for the manual injection while the automatic injection was carried out with 60 μl and 30 μl samples.

TABLE 1

| Serum sample | Disclosed values (±2 CV) meqv Cl/l | With dialysis Manual inj. 200 μl meqv Cl/l | With dialysis Autom. inj. 60 μl meqv Cl/l | Without dialysis Autom. inj. 30 μl Meqv Cl/l |
|---|---|---|---|---|
| Auto-ref | 102 ± 3 | 101 | — | — |
| Moni-trol I | 102 ± 3 | 102 | 102 | 102 |
| Moni-trol II | 116 ± 4 | 116 | 113 | — |
| Technicon SMA 2 | 103 | — | 105 | 105 |
| Pool | 101 | 103 | 101 | 99 |

As can be seen in the table, the chlorine measurement is at least as accurate with the automatic sample supply as with manual injection despite the fact that the sample amount can be reduced to almost a tenth.

Corresponding measurements have also been made with phosphorus and the results are presented in table 2.

TABLE 2

| Serum sample | Disclosed values (±2 CV) mg P/100 ml | Differential dilution manual injection 200 λl mg P/100 ml | With dialysis autom.injec. 100 λl mgP/100 ml |
|---|---|---|---|
| Auto-ref | 4.5 ± 0.3 | 4.0 | — |
| Moni-trol I | 3.4 ± 0.2 | 3.5 | 3.4 |
| Moni-trol II | 4.6 ± 0.3 | 4.3 | 5.0 |
| Technicon SMA 2 | 5.4 | — | 4.8 |
| Pool | 5.4 | 3.4 | 3.4 |

Analysis accuracy is fully equal to accuracy in manual injection here as well despite the fact that only half the sample amount was used.

What is claim is:

1. A method of supplying samples to a continuously flowing, non-segmented, unobstructed carrier solution for automatic analysis, comprising the steps of connecting a sampling conduit having a predetermined volume to a liquid sample supply and causing the liquid sample to occupy and fill said sampling conduit and thereby form a well-defined plug of known volume while said sampling conduit is disconnected from said flowing carrier solution, and automatically alternately disconnecting said sampling conduit from said supply while connecting said sampling conduit in a path of the flowing carrier solution which includes a shunt conduit having a much greater flow resistance than and parallel to said sampling conduit, and causing said carrier solution to flow through said sampling conduit and deliver said well-defined plug of sample to said path of flowing carrier solution.

2. A device for supplying samples to a continuously flowing, non-segmented, unobstructed carrier solution for automatic analysis, comprising a sample circuit including a liquid sample supply, and a sampling conduit having a predetermined volume connected to said liquid sample supply, a pump connected to said sample circuit and delivering liquid sample from said supply to said sampling conduit to fill said sampling conduit with a well-defined sample plug of known volume, a carrier flow circuit including a flow conduit, a pump connected to said flow conduit for delivering carrier liquid therethrough, valve means operable to connect said sampling conduit to said sample supply while disconnecting said sampling conduit from said carrier flow circuit, said valve means being operable to automatically alternately disconnect said sampling conduit from said sample supply while connecting said sampling conduit with said carrier flow circuit, said carrier flow circuit including a shunt conduit having a much greater flow resistance than and parallel to said sampling conduit, whereby when said valve means connects said sampling conduit to said carrier flow circuit, said carrier solution is caused to flow through said sampling conduit and delivers said sample to said carrier flow circuit.

3. A device according to claim 2 wherein said valve means is connected to the intake and discharge of said sampling conduit.

4. A device as defined in claim 2, wherein said shunt conduit is replaceable by a shunt conduit of different resistance to accommodate sampling conduits of different volumes.

* * * * *